(12) United States Patent
Amelotti et al.

(10) Patent No.: US 9,775,348 B2
(45) Date of Patent: Oct. 3, 2017

(54) COMPOSITION COMPRISING A SESTERTERPENE AND USE THEREOF AS ANTIBIOTIC AND ANTIFUNGAL ADJUVANT

(71) Applicant: RODE PHARMA S.R.L., Busto Arsizio (IT)

(72) Inventors: Luigi Amelotti, Busto Arsizio (IT); Lorenzo Secondini, Busto Arsizio (IT)

(73) Assignee: RODE PHARMA S.R.L., Busto Arsizio (VA) (IT)

( * ) Notice: Subject to any disclaimer, the term of this patent is extended or adjusted under 35 U.S.C. 154(b) by 0 days.

(21) Appl. No.: 14/408,553

(22) PCT Filed: Jun. 25, 2013

(86) PCT No.: PCT/IB2013/001360
§ 371 (c)(1),
(2) Date: Dec. 16, 2014

(87) PCT Pub. No.: WO2014/001882
PCT Pub. Date: Jan. 3, 2014

(65) Prior Publication Data
US 2015/0196029 A1 Jul. 16, 2015

(30) Foreign Application Priority Data
Jun. 25, 2012 (IT) ............................... MI2012A1109

(51) Int. Cl.
| | | |
|---|---|---|
| *A01N 37/00* | (2006.01) | |
| *A01N 57/00* | (2006.01) | |
| *A01N 37/08* | (2006.01) | |
| *A61K 45/06* | (2006.01) | |
| *A61K 31/122* | (2006.01) | |
| *A61K 31/19* | (2006.01) | |
| *A61K 31/56* | (2006.01) | |
| *A01N 35/06* | (2006.01) | |
| *A01N 43/653* | (2006.01) | |

(52) U.S. Cl.
CPC ............. *A01N 37/08* (2013.01); *A01N 35/06* (2013.01); *A01N 43/653* (2013.01); *A61K 31/122* (2013.01); *A61K 31/19* (2013.01); *A61K 31/56* (2013.01); *A61K 45/06* (2013.01)

(58) Field of Classification Search
IPC ............................................. A01N 37/00,57/00
See application file for complete search history.

(56) References Cited

U.S. PATENT DOCUMENTS

| | | | | |
|---|---|---|---|---|
| 5,190,979 A * | 3/1993 | Herman | ............... | C07D 323/02 424/DIG. 13 |
| 5,270,344 A * | 12/1993 | Herman | ............... | A61K 31/335 514/725 |
| 6,642,217 B2 * | 11/2003 | Krasutsky | ............... | C07J 63/008 514/169 |

OTHER PUBLICATIONS

Uttenweiler, A. et al., Molecular Biology of the Cell, vol. 18 pp. 166-175. Published 2007.*
Mutschler et al. (Drug Actions: Basic Principles and Therapeutic Aspects; 1995).*
Corriere et al. ("MRSA: An Evolving Pathogen", Disease-A-Month, 2008; 54(12):751-755).*
Li et al (J. Nat. Prod. vol. 58, pp. 74-81 published 1995).*
Annan et al (Journal of Science and Technology vol. 29, pp. 152-159 published 2009.*
PCT International Search Report mailed on Aug. 23, 2013 for PCT/IB2013/001360 filed on Jun. 25, 2013 in the name of Rode Pharma, S.R.L.
PCT Written Opinion mailed on Aug. 23, 2013 for PCT/IB2013/001360 filed on Jun. 25, 2013 in the name of Rode Pharma, S.R.L.
Baas et al, "Naturally occurring seco-ring-A-triterpenoids and their possible biological significance", Phytochemistry, vol. 24, No. 9, (1985), pp. 1875-1889.
Boeckman R.et al, "A total synthesis of gascardic acid, Journal of the American Chemical Society", ACS Publication, US, vol. 101, No. 17, 1 (1979), pp. 5060-5062.
Flekhter O B et al, "Synthesis of betulinic acid from botulin in extract and study of the antiviral and antiulcer activity of some related terpenoids", Pharmaceutical Chemistry Journal, vol. 36, No. 9, (2002). pp. 484-487.
Liu M et al, "Phytochemical and antifungal studies on *Terminalia mollis* and *Terminaia brachystemma*", Fitoterapia, vol. 80, No. 6, (2009), pp. 369-373.
Wang L. et al. "Sesterterpenoids" Nat. Prod. Rep., 2013, 30, pp. 455-473.
Leung, P. et at. "Ophiobolin A: A Natural Product Inhibitor of Calmodulin" The Journal of Biological Chemistry vol. 259, No. 5, Issue of Mar. 10, pp. 2742-2747, (1984).
Ma, L. et al.: "Preparation of Policosanol from Insect Wax by Reduction Method", *Chemistry and Industry of Forest Products*, Oct. 2009; vol. 29; No. 5; pp. 6-10 (Chinese original + English translation) Total of 16 pgs.
First Office Action for Chinese Patent Application No. 201380042898.2 filed on behalf of Rode Pharma S.R.L. Issue Date: Feb. 3, 2016. 12 pages (Chinese original + English translation).
Second Office Action for Chinese Patent Application No. 201380042898.2 filed on behalf of Rode Pharma S.R.L. dated Nov. 21, 2016. 10 pages, Chinese original + English translation.
Third Office Action for Chinese Patent Application No. 201380042898.2 filed on behalf of Rode Pharma S.R.L., dated Aug. 1, 2017. 10 pages. Chinese Original + English Translation.
Krizsan, K. et al. "Effect of the sesterterpene-type metabolites, ophiobilins A and B, on zygomycetes fungi" FEMS Microbiology Letters, Research letters, vol. 313, Oct. 2010, pp. 135-140.

* cited by examiner

*Primary Examiner* — Timothy Thomas
*Assistant Examiner* — George W Kosturko
(74) *Attorney, Agent, or Firm* — Steinfl + Bruno LLP

(57) ABSTRACT

The present invention relates to a composition comprising at least a sesterterpene for use as medicament like antibiotic or antifungal. Furthermore, the present invention relates to the use of at least a sesterterpene for increasing, assisting and/or enhancing the bacteriostatic and/or bactericidal activity of an antibiotic or the fungicidal activity of an antifungal compound.

15 Claims, No Drawings

COMPOSITION COMPRISING A SESTERTERPENE AND USE THEREOF AS ANTIBIOTIC AND ANTIFUNGAL ADJUVANT

CROSS REFERENCE TO RELATED APPLICATIONS

The present application is the US national stage of International Patent Application PCT/IB2013/001360 filed internationally on Jun. 25, 2013 which, in turn, claims priority to Italian Patent Application No. MI2012A001109 filed on Jun. 25, 2012.

The present invention relates to a composition comprising at least a sesterterpene for use as medicament like antibiotic or antifungal. Moreover, the present invention relates to the use of at least a sesterterpene for increasing, assisting and/or enhancing the bacteriostatic and/or bactericidal activity of an antibiotic or the fungicidal activity of an antifungal compound.

The adverse effects that can be elicited on the body by using, even over a short period, of drugs with antibiotic or fungicidal activity are known. For instance, antibiotics can remarkably decrease the gut bacterial flora and give rise, consequently, to alterations thereof with the risk of incurring in antibiotic-related diarrheas. Furthermore, antibiotics and antifungals may cause allergic reactions, toxicity in some body regions or intolerance caused by interaction with other drugs. Finally, a long-term use of antibiotics or antifungals may increase the risk, for example, of antibiotic resistance by the pathogenic bacteria themselves. This drawback may also arise as a consequence of a sustained use of drugs with fungicidal activity. This occurs because bacteria mutate to more resistant strains such as for example *Staphylococcus aureus* MRSA (methycillin resistant).

Therefore, all the professionals in the field agree with generally reducing the use of drugs and, in particular, antibiotics and/or antifungals. Specifically, it would be desirable to reduce the antibiotic amounts administered to patients in order to minimize the adverse effects and, at the same time, avoid the abuse of these substances, preventing the risk of antibiotic resistance increase. An indiscriminate use of drugs with fungicidal activity should be also always avoided, for preventing both the side effects of these substances, and mainly the resistance phenomena.

Therefore, there is a need to have a natural substance with bacteriostatic and/or bactericidal and/or fungicidal activity, devoid of the above-mentioned side effects, which can be used in place of or as an alternative of antibiotics or antifungals presently used in the state of the art; or which can be used along with reduced doses of antibiotics or antifungal.

The antibiotic or antifungal abuse and, consequently, the related risk of resistance could be thereby reduced.

Particularly, there is a need to use the existing antibiotics and antifungals at reduced concentrations or, alternatively, on equal concentration specified/recommended for each specific commercially available antibiotic or antifungal, increase their bacteriostatic and/or bactericidal activity or increase the fungicidal activity of commercially available antifungals, thereby reducing the adverse effects.

The Applicant conducted an intensive research activity through which selected, starting from a wide number of compounds and natural extracts belonging to the chemical family of terpenes, some specific and selected compounds or mixtures/combinations thereof. In particular, the Applicant selected some compounds and extracts belonging to sesterterpene (sesterpenes —C25) and triterpene families since these compound groups have shown to be able to address the above-mentioned needs.

It is an object of the present invention the sesterterpenes selected from the group comprising or, alternatively, consisting of Ophiobolin A, Ophiobolin B, gascardic acid and ceroplastol for use as medicament in the treatment of gram-positive and/or gram-negative bacteria and/or fungi.

It is an object of the present invention the sesterterpenes selected from the group comprising or, alternatively, consisting of Ophiobolin A, Ophiobolin B, gascardic acid and ceroplastol, for use as antibiotic adjuvant (for increasing and/or assisting and/or enhancing the bacteriostatic and/or bactericidal activity of a commercially available antibiotic) for treating gram-positive and/or gram-negative bacteria or infections caused therefrom; or for use as antifungal adjuvant (for increasing and/or assisting and/or enhancing the fungicidal activity of a commercially available antifungal) for treating fungi or infections caused therefrom.

In a preferred embodiment, said sesterterpene is administered in combination with an antibiotic or antifungal (simultaneous administration). This simultaneous administration is carried out by administering a composition alone which comprises said sesterterpene and said known antibiotic or antifungal.

Alternatively, said simultaneous administration is carried out by administering two compositions, the former comprising said sesterterpene and the latter comprising said known antibiotic or antifungal.

Alternatively, said sesterterpene and said known antibiotic or antifungal are not administered simultaneously but at different times each other, sequentially, (separate and non-concurrent administration), for example the administration of said sesterterpene and said antibiotic or antifungal may occur in a range of time within 1 to 60 minutes, preferably 5 to 30 minutes.

It is an object of the present invention a composition for use as medicament which comprises or, alternatively, consists of at least a sesterterpene selected from the group comprising or, alternatively, consisting of Ophiobolin A, Ophiobolin B, gascardic acid and ceroplastol, for the treatment of gram-positive and/or gram-negative bacteria and/or fungi or infections caused therefrom.

It is an object of the present invention a composition which comprises or, alternatively, consists of at least a sesterterpene selected from the group comprising or, alternatively, consisting of Ophiobolin A, Ophiobolin B, gascardic acid and ceroplastol combined with a commercially available antibiotic to use as adjuvant of said antibiotic, for increasing and/or assisting and/or enhancing the bacteriostatic and/or bactericidal activity of said antibiotic thereby reducing the employed and/or recommended dose thereof.

It is an object of the present invention a composition which comprises or, alternatively, consists of at least a sesterterpene selected from the group comprising or, alternatively, consisting of Ophiobolin A, Ophiobolin B, gascardic acid and ceroplastol combined with a commercially available antifungal to use as adjuvant of said antifungal, for increasing and/or assisting and/or enhancing the activity of said antifungal thereby reducing the employed and/or recommended dose thereof.

Preferred forms of the present invention will be evident from the detailed description below.

Following to an intense research activity, the Applicant found that sesterterpenes (sesterpenes C25) selected from the group comprising or, alternatively, consisting of Ophiobolin A, Ophiobolin B, gascardic acid and ceroplastol have a bacteriostatic and/or bactericidal and/or fungicidal activity allowing them to be used as a medicament in the treatment of-gram-positive and/or gram-negative bacteria and/or fungi or, alternatively, as antibiotic and antifungal adjuvants.

Sesterterpenes being used are obtained preferably in the form of natural extract, as set forth below. The sesterterpenes being used are selected from the group comprising or, alternatively, consisting of Ophiobolin A, Ophiobolin B, gascardic acid and ceroplastol. Sesterterpenes are derived from geranylfarnesol pyrophosphate and contain 25 carbon atoms (C25). The sesterterpenoid structure has been reported in Wang L et al., *Nat prod Rep* 2013, 30, 455; Leung P C et al., *J Biol Chem* 1984, 259, 2742-7). In a preferred embodiment, ophiobolin A $C_{25}H_{36}O_4$ has CAS 4611056, ophiobolin B $C_{25}H_{36}O_4$ has CAS 5601741 and ceroplastol $C_{25}H_{40}O$ has CAS 18674-12-9.

Sesterterpenes are non-toxic and well-tolerated within the body. Advantageously, gascardic acid or a salt thereof or their derivatives, being devoid of typical antibiotic and antifungal side effects, can be used in place of or as an alternative of antibiotics and/or antifungals.

In the composition of the present invention, gascardic acid or another sesterterpene (or a salt or derivative thereof) among those above-mentioned can be used along with doses reduced from 10 to 80%, preferably from 25 to 75% or even more preferably from 30 to 50%, of said know antibiotics or antifungals since the above cited gascardic acid and sesterterpenes, in particular the gascardic acid, have shown to be able of increasing and/or assisting and/or enhancing the bacteriostatic and/or bactericidal activity or efficacy of antibiotics, or the fungicidal activity or efficacy of antifungals.

It is an object of the present invention a pharmaceutical composition or a supplement product comprising or, alternatively, consisting of gascardic acid and/or a salt thereof or their derivatives, for use in the treatment of gram-positive and/or gram-negative bacteria and/or fungi.

In a preferred embodiment, said composition comprises or, alternatively, consists of gascardic acid and at least a sesterterpene selected from ophiobolin A, ophiobolin B and ceroplastol, for use in the treatment of gram-positive and/or gram-negative bacteria and/or fungi.

It is an object of the present invention a pharmaceutical composition or a supplement product comprising or, alternatively, consisting of gascardic acid and/or a salt thereof or their derivatives, combined with an antibiotic drug, for use in the treatment of gram-positive and/or gram-negative bacteria or infections caused therefrom.

In a preferred embodiment, said composition comprises or, alternatively, consists of gascardic acid and at least a sesterterpene selected from ophiobolin A, ophiobolin B and ceroplastol, combined with an antibiotic, for use in the treatment of gram-positive and/or gram-negative bacteria or infections caused therefrom.

It is an object of the present invention a pharmaceutical composition or a supplement product comprising or, alternatively, consisting of gascardic acid and/or a salt thereof or their derivatives, combined with an antifungal, for use in the treatment of fungi or infections caused therefrom.

In a preferred embodiment, said composition comprises or, alternatively, consists of gascardic acid and at least a sesterterpene selected from ophiobolin A, ophiobolin B and ceroplastol, combined with an antifungal, for use in the treatment of fungi or infections caused therefrom.

In the context of the present invention when referring to a "composition" we mean to include a pharmaceutical composition or a supplement product, without limitations, but merely in order to facilitate the description. The composition (a pharmaceutical composition or supplement product) may be in solid or liquid form or suspension or emulsion.

Sesterterpenes such as for example gascardic acid are prepared and used in the present composition in the form of alcoholic or hydroalcoholic extract. The alcohol being used can be selected from ethyl or propyl or butyl or pentyl alcohol. The hydroalcoholic solvent consists of water and alcohol in a weight ratio comprised from 1:10 to 10:1, preferably from 1:5 to 5:1 or from 1:3 to 3:1, preferably from 1:2 to 2:1 or 1:1; for example it can comprise a hydroalcoholic extract containing 80% by weight of water and 20% by weight of alcohol, for example 90% or 80% or 70% or 60% or 50% by weight of water and 10% or 20% or 30% or 40% or 50%% by weight of ethyl alcohol.

Preferably, the alcoholic or hydroalcoholic extract has a gascardic acid or ophiobolin A or ophiobolin B or ceroplastol concentration (or their salts or derivatives thereof) comprised from 1 to 20%, preferably 3 to 15%, even more preferably 5 to 10%.

Alternatively, the gascardic acid or ophiobolin A or ophiobolin B or ceroplastol (or their salts or derivatives thereof) exists in the composition in the form of aqueous extract at a concentration comprised from 1 to 20%, preferably from 3 to 15%, even more preferably from 5 to 10%.

The gascardic acid is extracted from the following substrates selected from *Teminalia, Melia volkensii, Scytalidium acidophilum, Cochlibolus heterostropus* and *Haslea ostrearia;* preferably from *Terminalia*, a tree from Combretaceae family.

Species of genus *Terminalia* which can be used in the present invention are selected from the group comprising or, alternatively, consisting of: *Terminalia alata (T. elliptica, T. tomentosa), Terminalia arborea (T. citrina), Terminalia australis*-Palo amarillo, *Terminalia bellirica (Myrobalanus bellirica), Terminalia brassii, Terminalia brownii, Terminalia calamansanai, Terminalia chebula (T. reticulata), Terminalia citrina, Terminalia edulis (T. microcarpa), Terminalia ferdinandiana, Terminalia glaucifolia, Terminalia ivorensis, Terminalia oblongata, Terminalia schimperiana, Terminalia tetrandra, Terminalia volucris.*

*Terminalia* is used in the form of crushed, flaked or triturated material, such as bark or leaves. Gascardic acid can be also extracted from algae or fungi, for example from fungi belonging to the genus *Malassezia*.

The extraction of sesterterpenes, such as for example gascardic acid or a salt thereof or their derivatives, is conducted by using processes and equipment well-known to the person skilled in the field. For example, extraction at temperature comprised from 40 to 100° C. by using a solvent such as for example water or alcohol or a mixture comprising water and alcohol can be used. For example, a steam extraction can be used.

When using water as solvent, preferably distilled water, the extraction is carried out at pH comprised from 7 to 9, preferably at pH 8, by using a base or it is carried out at pH comprised from 1 a 4, preferably at pH 2, by using an acid.

For example, 1 Kg of dry *Terminalia* (e.g., *Terminalia ivorensis*) as crushed, flaked or triturated material, being extracted by 1 liter of solvent selected from those above-mentioned, yields an extract containing gascardic acid at a concentration comprised from 3 to 10%.

Basically, following to extraction, an emulsion or suspension containing gascardic acid or a derivative thereof is obtained, being then evaporated until a solid residual containing gascardic acid or its derivatives is attained.

By "gascardic acid derivative" is meant to comprise, in the context of the present invention, compounds or chemical molecules or aggregates of compounds having a chemical and/or functional structure similar to gascardic acid itself, gascardic acid precursors, such as for example geranyl pyrophosphate or geranylfarnesol pyrophosphate, or metabolites thereof.

By "gascardic acid salt" is meant a salt derived from gascardic acid with a monovalent, bivalent or trivalent cation to yield a compound soluble or partially soluble in water or alcohol or their mixtures. The same applies to the other above-mentioned sesterterpenes.

The composition for use as medicament comprising or, alternatively, consisting of gascardic acid or a salt thereof or their derivatives has a bacteriostatic and/or bactericidal and/or fungicidal activity. The bacteriostatic and/or bactericidal activity is exerted against gram-positive and/or gram-negative bacteria.

The bacteriostatic and/or bactericidal activity is preferably exerted against gram-positive bacteria belonging to the genus: *Staphylococcus*, preferably to the species *Staphylococcus aureus, Staphylococcus aureus* subsp. *rosen* and *Staphylococcus epidermidis;* against bacteria belonging to the genus *Pseudomonas,* preferably to the species *Pseudomonas aeruginosa;* against gram-negative bacteria belonging to the species *Escherichia coli;* against gram-positive bacteria belonging to the genus *Bacillus,* preferably to the species *Bacillus cereus;* against bacteria belonging to the species *Proteus vulgaris, Legionella, Salmonella, Listeria monocytogenes, Clostridium difficile, Streptococcus pyogenes, Enterococcus fecalis, Enterococcus hirae, Klebsiella pneumonia.*

The Applicant successfully tested the bacteriostatic and/or bactericidal activity against: *Staphylococcus aureus* subsp. *rosen*, ATCC 25923; *Staphylococcus epidermidis*, ATCC 12228 and ATCC 35984; *Bacillus cereus*, ATCC 14579; *Proteus vulgaris*, ATCC 29906; *Legionella* ATCC 33152; *Escherichia coli*, ATCC 25922, ATCC 35218, ATCC 8739, ATCC 11229 and ATCC 13706; *Salmonella, ATCC* 14028; *Listeria monocytogenes*, ATCC 15313; *Clostridium difficile*, ATCC 43255; *Streptococcus pyogenes*, ATCC 19615; *Enterococcus fecalis*, ATCC 29212; *Enterococcus hirae*, ATCC 10541; *Klebsiella pneumoniae*, ATCC 13883; *Pseudomonas aeruginosa*, ATCC 9027 and ATCC 27853.

The antifungal activity is preferably exerted against fungi belonging to the genus Aspergillus, preferably to the species *Aspergillus niger, Aspergillus versicolor* and *Aspergillus clavatus;* against *Candida albicans;* against fungi belonging to the genus *Trichoderma,* preferably against the species *Trichoderma viride* and *Trichoderma viridescens;* against fungi belonging to the species *Penicillium funicolosum, Chaetoimium globosum, Fusarium rubrum, Fusarium oxysporum, Fusarium solani, Pullularia fermantans* and *Rhizopus* spp.

The Applicant successfully tested the fungicidal activity against: *Aspergillus niger*, ATCC 16404; *Aspergillus versicolor*, ATCC 11730, *Aspergillus clavatus*, ATCC 1007; *Trichoderma viride*, ATCC 28020; *Penicillium funicolosum*, ATCC 9644; *Chaetoimium globosum*, ATCC 16021; *Fusarium rubrum*, ATCC 42690; *Fusarium oxysporum*, ATCC 7601; *Fusarium solani*, ATCC 36031; *Pullularia fermantans*, ATCC 12537 and *Rhizopus* spp., ATCC 34612.

In a preferred embodiment, said composition comprises or, alternatively, consists of at least a sesterterpene selected from the group comprising or, alternatively, consisting of Ophiobolin A, Ophiobolin B, gascardic acid and ceroplastol combined with betulinic acid (triterpene) or a salt thereof or their derivatives, for use in the treatment of gram-positive and/or gram-negative bacteria and/or fungi or, alternatively, for use as antibiotic or antifungal adjuvant.

It is an object of the present invention a pharmaceutical composition or a supplement product comprising or, alternatively, consisting of gascardic acid and/or a salt thereof or their derivatives combined with betulinic acid or a salt thereof or their derivatives, for use in the treatment of gram-positive and/or gram-negative bacteria and/or fungi.

It is an object of the present invention a pharmaceutical composition or a supplement product comprising or, alternatively, consisting of gascardic acid and/or a salt thereof or their derivatives combined with betulinic acid or a salt thereof or their derivatives, in combination with an antibiotic drug, for use in the treatment of gram-positive and/or gram-negative bacteria.

It is an object of the present invention a pharmaceutical composition or a supplement product comprising or, alternatively, consisting of gascardic acid and/or a salt thereof or their derivatives combined with betulinic acid or a salt thereof or their derivatives, in combination with an antifungal, for use in the treatment of fungi.

Preferably, said gascardic and betulinic acids or their derivatives exist in said composition in a weight or volume ratio comprised from 1:5 to 5:1, preferably in a weight or volume ratio from 1:3 to 3:1, for example 1:1 by weight or volume.

The betulinic acid is prepared and used in the present composition in the form of alcoholic or hydroalcoholic extract. The alcohol being used can be selected from ethyl or propyl or butyl or pentyl alcohol.

The hydroalcoholic solvent consists of water and alcohol in a weight ratio comprised from 1:10 to 10:1, preferably from 1:5 to 5:1 or from 1:3 to 3:1, preferably from 1:2 to 2:1 or 1:1; for example it can comprise a hydroalcoholic extract containing 80% by weight of water and 20% by weight of alcohol, for example 90% or 80% or 70% or 60% or 50% by weight of water and 10% or 20% or 30% or 40% or 50% by weight of ethyl alcohol.

Preferably, the alcoholic or hydroalcoholic extract has a concentration of betulinic acid or its derivatives comprised from 1 to 20%, preferably from 3 to 15%, even more preferably from 5 to 10%.

Alternatively, betulinic acid or its derivatives exists in the composition in the form of aqueous extract at a concentration comprised from 1 to 20%, preferably from 3 to 15%, even more preferably from 5 to 10%.

Betulinic acid is extracted preferably from *Betula cortex, Betula pendula roth, Glycyrriza glabra* and *Betula papyrifer* by using processes and equipment well-known to the person skilled in the field.

In another preferred embodiment, said composition comprises or, alternatively, consists of at least a sesterterpene selected from the group comprising or, alternatively, consisting of Ophiobolin A, Ophiobolin B, gascardic acid and ceroplastol combined with a pentacyclic triterpene steroid such as friedelin or a salt thereof or their derivatives, for use in the treatment of gram-positive and/or gram-negative bacteria and/or fungi or, alternatively, for use as antibiotic or antifungal adjuvant.

It is an object of the present invention a pharmaceutical composition or a supplement product comprising or, alternatively, consisting of gascardic acid and/or a salt thereof or their derivatives combined with friedelin or a salt thereof or their derivatives, for use in the treatment of gram-positive and/or gram-negative bacteria and/or fungi.

It is an object of the present invention a pharmaceutical composition or a supplement product comprising or, alternatively, consisting of gascardic acid and/or a salt thereof or their derivatives combined with friedelin or a salt thereof or their derivatives, in combination with an antibiotic drug, for use in the treatment of gram-positive and/or gram-negative bacteria.

It is an object of the present invention a pharmaceutical composition or a supplement product comprising or, alternatively, consisting of gascardic acid and/or a salt thereof or their derivatives combined with friedelin or a salt thereof or their derivatives, in combination with an antifungal drug, for use in the treatment of fungi.

Preferably, said gascardic acid and said friedelin or their salts or derivatives exist in said composition in a weight or volume ratio comprised from 1:5 to 5:1, preferably in a weight or volume ratio from 1:3 to 3:1, for example 1:1 by weight or volume.

Friedelin is prepared and used in the present composition in the form of alcoholic or hydroalcoholic extract. The alcohol being used can be selected from ethyl or propyl or butyl or pentyl alcohol.

The hydroalcoholic solvent consists of water and alcohol in a weight ratio comprised from 1:10 to 10:1, preferably from 1:5 to 5:1 or from 1:3 to 3:1, preferably from 1:2 to 2:1 or 1:1; for example it can comprise a hydroalcoholic extract containing 80% by weight of water and 20% by weight of alcohol, for example 90% or 80% or 70% or 60% or 50% by weight of water and 10% or 20% or 30% or 40% or 50% by weight of ethyl alcohol.

Preferably, the alcoholic or hydroalcoholic extract has a concentration of friedelin or its derivatives comprised from 1 to 20%, preferably from 3 to 15%, even more preferably from 5 to 10%.

Alternatively, the betulinic acid or a salt thereof or their derivatives exists in the composition in the form of aqueous extract at a concentration comprised from 1 to 20%, preferably from 3 to 15%, even more preferably from 5 to 10%.

Friedelin is preferably extracted from *Pilose asiabell, Sughero nero, Terminalia avicennioides* and *Eugenia chloratia* by using processes and equipment well-known to the person skilled in the field.

In another preferred embodiment, said composition comprises or, alternatively, consists of at least a sesterterpene selected from the group comprising or, alternatively, consisting of Ophiobolin A, Ophiobolin B, gascardic acid and ceroplastol combined with betulinic acid or a salt thereof or their derivatives and friedelin or a salt thereof or their derivatives, for use in the treatment of gram-positive and/or gram-negative bacteria and/or fungi or, alternatively, for use as antibiotic or antifungal adjuvant.

It is an object of the present invention a pharmaceutical composition or a supplement product comprising or, alternatively, consisting of gascardic acid and/or a salt thereof or their derivatives combined with betulinic acid or a salt thereof or their derivatives and friedelin or a salt thereof or their derivatives, for use in the treatment of gram-positive and/or gram-negative bacteria and/or fungi.

It is an object of the present invention a pharmaceutical composition or a supplement product comprising or, alternatively, consisting of gascardic acid and/or a salt thereof or their derivatives combined with betulinic acid or a salt thereof or their derivatives and friedelin or a salt thereof or their derivatives, in combination with an antibiotic drug, for use in the treatment of gram-positive and/or gram-negative bacteria.

It is an object of the present invention a pharmaceutical composition or a supplement product comprising or, alternatively, consisting of gascardic acid and/or a salt thereof or their derivatives combined with betulinic acid or a salt thereof or their derivatives and friedelin or a salt thereof or their derivatives, combined with an antifungal, for use in the treatment of fungi.

Preferably, said gascardic and betulinic acids and said friedelin or their sans or derivatives exist in said composition in a 1:1:1 weight ratio by weight or volume.

When using gascardic acid as antibiotic adjuvant, the composition further comprises an antibiotic.

Advantageously, the gascardic acid or a salt thereof or their derivatives can be used with doses reduced from 10 to 80%, preferably from 20 to 60%, of said antibiotics or antifungals since gascardic acid or a salt thereof or their derivatives have shown to be able to increase and/or assist and/or enhance the bacteriostatic and/or bactericidal activity of antibiotics or the fungicidal activity of antifungals. The adjuvant effect of the composition of the present invention has been successfully tested to the following fungicides: fluconazole, isoconazole, miconazole, ketoconazole, abafungin (CAS 129639-79-8), caspofungin micafungin. Preferably, said antibiotic is selected from those below-mentioned.

It is an object of the present invention a composition comprising or, alternatively, consisting of gascardic acid or derivatives thereof and an antibiotic, for use as adjuvant of said antibiotic (for increasing, assisting and/or enhancing the bacteriostatic and/or bactericidal and/or fungicidal activity of an antibiotic or antifungal) in the treatment of gram-positive and/or gram-negative bacteria and/or fungi.

The antibiotic is preferably selected from the group comprising the following compound families.

i) Penicillins also referred to as "beta-lactam antibiotics" and used in the treatment of many kinds of bacterial infection. Common penicillin-family antibiotics include: benzylpenicillin (Penicillin G), amoxicillin (Amox) and ampicillin (Polycillin). Amoxicillin is often combined with clavulanic acid (a penicillinase inhibitor).

ii) Tetracyclines, are a class of broad-spectrum antibiotics which act by inhibiting the protein synthesis in sensitive bacteria. Tetracyclines comprise: Doxycycline (Vibramycin.), minocycline, (Minocin) and tetracycline (Sumycin.).

iii) Macrolides, are a class of antibiotics also known as "polyketide antibiotics". They act by inhibiting the protein synthesis in bacteria, similarly to other different antibiotic classes. Macrolides are commonly used for treating infections due to Gram-positive bacteria (for example, Streptococcus pneumoniae). Common macrolides include: azithromycin (Zithromax), erythromycin (Vancomycin) and clarithromycin (Biaxin).

iv) Cotrimoxazole, sulfonamides and trimethoprim. Common names for cotrimoxazole include: Bactrim, Septra and Sulfatrim.

v) Cephalosporins, are another group of beta-lactam antibiotics, and are structurally related to penicillins. Contrary to penicillins, cephalosporins are effective against a broader range of bacteria. Common cephalosporins include: cephalexin (Keflex), cefadroxil (Duricef) and cefixime (Suprax).

vi) Quinolones, are effective against gram-negative and gram-positive bacteria. Common quinolones include: ciprofloxacin (Cipro), levofloxacin (Levaquin) and moxifloxacin (Avelox).

vii) Rifamycins, such as rifampicin (Rifampicin), rifabutin (Mycobutin) and rifapentine (Priftin).
viii) Aminoglycosides, are effective against gram-negative bacteria. Common aminoglycosides include: neomycin (Neosporin), amikacin (Amikin) and tobramycin (Tobrex).

Additional common antibiotics are clindamycin, dapsone, mupirocin, bacitracin, chloramphenicol, daptomycin.

Compositions of the present invention, for use as medicament, can also envisage the presence of at least another compound selected among sesterpenes selected from the group comprising or, alternatively, consisting of:
(i) linear sesterpenes, said linear sesterpenes are preferably selected from the group comprising or, alternatively, consisting of farnesyl geraniol, farnesylnerole, furospongin-3, ircinin-1;
(ii) monocyclic sesterpenes, said monocyclic sesterpenes are preferably selected from the group comprising or, alternatively, consisting of monohalide, urea peroxide and cochliobolin A.
(iii) bicyclic sesterpenes, said bicyclic sesterpenes are preferably selected from the group comprising or, alternatively, consisting of 11-epitepestacin and beta-nitropropionic acid.
(iv) tricyclic sesterpenes, preferably is genepolide.
(v) tetracyclic sesterpenes, said tetracyclic sesterpenes are preferably selected from the group comprising or, alternatively, consisting of scalarin and hyrtisin A.
(vi) pentacyclic sesterpenes, said pentacyclic sesterpenes are preferably selected from the group comprising or, alternatively, consisting of astellatol-B, hunlactone, prianosin-A and prianosin-B.
(vii) norsesterpenes, said norsesterpenes are preferably selected from the group comprising or, alternatively, consisting of prianicin-A and prianicin-B.

In an embodiment, the composition for use as medicament may also envisage the presence of, in combination with gascardic acid and/or friedelin and/or betulinic acid, at least another compound selected among sesterpenes selected from the group comprising or, alternatively, consisting of: ophiobolins and their derivatives, preferably ophiobolin A (CAS 4611-05-6) or ophiobolin B; pimaric acid (CAS 127-27-5) and its derivatives; geranylfarnesol (CAS 79577-58-5) and its derivatives; ceroplastol and its derivatives. The invention will be also described through the following experimental part.

Experimental Part
1. Bacteriostatic Tests Using Gascardic Acid

A study about the efficacy of a gascardic acid-based composition referred to as M3 was conducted against some publicly available pathogenic bacteria such as (1) *Staphylococcus aureus*—ATCC 25923 ($190 \times 10^6$ UFC/ml) (2) *Pseudomonas aeruginosa*—ATCC 15442 ($305 \times 10^6$ UFC/ml) and (3) *Escherichia coli*—ATCC 25922 ($300 \times 10^6$ UFC/ml). The composition M3 was tested according to MIC method.

The method was carried out as follows. Time by time, a culture of the above-mentioned strains was prepared in a Tryptic soy Agar type growth medium. Freshly-made subcultures were prepared, and incubated until obtaining an estimated density of $1 \times 10^6$ cells per ml of culture. The assessment was obtained by spectrophotometric measurement of absorption at known wavelengths.

The bacteriostatic tests were performed by placing the bacterial culture in Petri dishes with a central well of 1 cm diameter, containing the 2 cc aliquot of composition M3. Then, the freshly-made subculture was plated over the surrounding medium. Next, the Petri dishes were placed in a thermostatic environment at 30° C. and examined after 24 and 48 ore.

The results are expressed as inhibition halo diameter measured over each Petri dish. The diameter does not include the 10 mm central well. Consequently, a zero mm (0 mm) diameter denotes an undetectable halo. The given average values are obtained by considering the minimum and maximum value of each halo.

Table 1 shows that a gascardic acid-based composition (2 cc of a 0.7% solution equal to 35 mg) has bacteriostatic activity against the tested pathogenic bacteria.

Brief Description of MIC Method

The composition M3 has been tested by assessing the Minimum Inhibitory Concentration (MIC) i.e. the lowest concentration of an antimicrobial substance (such as for example an antibiotic) capable to inhibit the bacterial growth. MIC is assessed by testing in vitro a standard bacterial concentration with a series of stepwise dilutions of antibiotic. By the dilution method the bacterial resistance to a single antibiotic at decreasing concentrations is evaluated, helpful for calculating the lower antibiotic concentration capable to inhibit the bacterial growth. The bacterial concentration is proportional to turbidity.

Preparation of test tubes. A series of test tubes containing a liquid supplemented growth medium (for example 9.9 ml per test tube) are prepared. Next, a serial dilution of the examined antibiotic is obtained. For this purpose, 0.1 ml of antibiotic agent is poured in the first test tube. Then, the test tube content is mixed and 0.1 ml of medium-antibiotic from the first test tube are collected and poured in the second test tube. Now, after mixing again the second test tube content, 0.1 ml of medium-antibiotic from the second test tube are collected and poured in the third test tube. And so forth until the last test tube. At this stage, a series of test tubes having decreasing antibiotic concentrations (decimals) are obtained.

Inoculation. Now the examined inoculum has to be seeded. The inoculum is prepared starting from a bacterial culture grown at 37° C. over 24 hours. The seeding needs to be carried out with a sustained amount of inoculum per test tube. The bacterial concentration in the inoculum is about $1 \times 10^6$ cells per ml. Incubation and reading. The seeded test tubes are incubated at 37° C. over 24 hours. After that period, the turbidity in each test tube is evaluated, confirming the bacterial culture growth. The test tubes at higher turbidity are those with a lower concentration of antibiotic. The medium turbidity decreases in presence of greater antibiotic concentrations.

2. Bacteriostatic Tests Using Gascardic Acid and Antibiotic.

According to the above-described MIC method, a test where the pathogenic bacteria (1) *Staphylococcus aureus* ATCC 25923 (2) *Pseudomonas aeruginosa* ATCC 15442 and (3) *Escherichia coli* ATCC 25922 were tested along using composition M5 and composition M5+M3 was conducted.

Composition M5 consists of 2 cc of [Amoxicillin+Clavulanic Acid] solution 1000 mg (Amoxicillin 875 mg and Clavulanic Acid 125 mg), test A.

Composition M5+M3 consists of 1 cc of [Amoxicillin+Clavulanic Acid] solution as above, and 1 cc of Gascardic acid solution (0.7% equal to 35 mg), test B.

Table 2 confirms that the composition comprising gascardic acid is able to increase the antibiotic efficacy and create a synergistic effect with antibiotics. The result demonstrates that gascardic acid allows to reducing the antibiotic amount being used while obtaining the same efficacy.

Advantageously, the antibiotic concentration can be reduced from ⅓ to ⅔. Advantageously, in many cases with a broad range of antibiotics, the antibiotic concentration can be reduced of about 50%.

TABLE 1

| Pathogenic bacteria | Halo in "mm" |
|---|---|
| (1) *Staphylococcus aureus* ATCC 25923 | 8 |
| (2) *Pseudomonas aeruginosa* ATCC 15442 | 6 |
| (3) *Escherichia coli* ATCC 25922 | 6 |

TABLE 2

| | Test | |
|---|---|---|
| | Test A | Test B |
| Composition | M5 | M5 + M3 |
| Total volume | 2 cc | 1 cc + 1 cc |
| (1) *Staphylococcus aureus* ATCC 25923 | 19 | 19 |
| (2) *Pseudomonas aeruginosa* ATCC 15442 | 7 | 12 |
| (3) *Escherichia coli* ATCC 25922 | 10 | 10 |

FUNGAL TESTS

A study about the efficacy of the composition of the present invention to some fungi was conducted. The compositions were tested according to the MIC method. The methodology being used is herein reported.

1) Test Preparation

The tested fungi strains were as follows: i) *Aspergillus niger*, ATCC 16404; ii) *Trichoderma viride*, ATCC 28020; iii) *Penicillium funiculosum* ATCC 9644 and iv) *Chaetomium globosum*, ATCC 16021.

For each strain, time by time, a culture in liquid nutrient medium such as SABORAUD DEXEROSE AGAR was made.

Freshly-made subcultures were created, and incubated until obtaining an estimated density of 10 cells per ml. The estimate was obtained by spectrophotometric measurement of absorption at 530 nm.

Bacteriostatic tests: The tests were performed by placing fungal culture aliquots (set forth in the tables below) in Petri dishes with a central well (1 centimeter diameter) in which the product to be tested was poured. All the plates were incubated at 25° C. The incubation time for solutions A, B, C, D, E and F was 72 hours, while for products. M1, M2 and M3 the time was 30 hours.

2) Minimum Inhibitory Concentration (MIC) Assessment

The following compound were considered:
SAMPLE M1: Betulinic acid solution.
SAMPLE M2: Fridelin solution
SAMPLE M3: Gascardic acid solution
SAMPLE M4: Fluconazole (well-known fungicide) solution For M1, M2 and M3 solutions of 7% compound in 99% ethyl alcohol 100 ml were prepared. 1 ml of these solutions was collected (0.07 mg of compound).

For M4 a solution of 200 mg fluconazole/99% ethyl alcohol 100 ml was prepared. 1 ml of this solution was collected (2 mg of fluconazole).

| Test No: | Tested solution | Total volume of inoculum per plate |
|---|---|---|
| Test A | M4 | 1 cc |
| Test B | M4 1 cc + M1 1 cc | 1 cc of mixture |
| Test C | M4 1 cc + M2 1 cc | 1 cc of mixture |
| Test D | M4 1 cc + M3 1 cc | 1 cc of mixture |
| Test E | M1 0.5 cc + M2 0.5 cc + M3 0.5 cc | 1 cc of mixture |
| Test F | M4 0.25 cc + M1 0.41 cc + M2 0.41 cc + M3 0.41 cc | 1 cc of mixture |
| Test M1 | M1 | 1 cc |
| Test M2 | M2 | 1 cc |
| Test M3 | M3 | 1 cc |

3) Results from Bacteriostatic Tests

The results are expressed as inhibition halo diameter being measured over each plate. The diameter does not include the 10 mm central well or the paper. Consequently, a 0 mm diameter denotes an undetectable halo. The described values indicate the average from the minimum and maximum values of halos for each test. Values are expressed in mm of inhibition.

| Tests with well | *Aspergillus niger* | *Trichoderma viride* | *Penicillium funiculosum* | *Chaetomium globosum* |
|---|---|---|---|---|
| Test A | 1 | 0 | 0 | 11-17 |
| Test B | 1-2 | 32-35 (*) | 3-5 | 16-19 |
| Test C | 0 | 0 | 0 | 10-14 |
| Test D | 2-4 | 13-31 (*) | 4-6 | 17-22 |
| Test E | 2-4 | 31-34 (*) | 5-9 | 13-24 |
| Test F | 1-2 | 32-34 (*) | 4-6 | 10-22 |
| Test M1 | 15-16 | 31-34 (*) | 12-18 (*) | 22-26 |
| Test M2 | 3-4 | 2-6 | 1-1.5 | 5-11 (*) |
| Test M3 | 15-18 | 16-27 | 15-20 (*) | 19-26 |
| | mm of inhibition | mm of inhibition | mm of inhibition | mm of inhibition |

(*) within the inhibition halo there is less developed mycelium

The obtained results show that the tested solutions M1, M2 and M3 alone or combined with each other exert a strong fungicidal activity than M4 (fluconazole) if considering that they were tested at a 0.07 mg versus 2 mg value (about 1:28 ratio)

The invention claimed is:

1. A method for treating a subject, the method comprising: administering to the subject a terpene selected from the group consisting of gascardic acid and a salt thereof, geranyl pyrophosphate and geranylfarnesol pyrophosphate in an effective amount to treat bacteria, fungi or infections caused therefrom in the subject, wherein the bacteria are selected from the group consisting of *Staphylococcus aureus, Staphylococcus aureus* subsp *rosen* and *Staphylococcus epidermidis, Pseudomonas, Escherichia coli, Bacillus, Proteus vulgaris, Legionella, Salmonella, Listeria monocytogenes, Clostridium difficile, Streptococcus pyogenes, Enterococcus fecaiis, Enterococcus hirae,* and *Kiebsielia pneumoniae*; and the fungi are selected from the group consisting of *Aspergillus niger, Aspergillus versicolor* and *Aspergillus clavatus, Candida albicans, Trichoderma, Peniciiiiurn funirolosum, Chaetoimium giobosum, Fusarium rubrum, Fusarium oxysoorum, Fusarium solani, Puliularia fermantans* and *Rhizoous* spp.

2. The method of claim 1, wherein said terpene is combined with an antibiotic for increasing a bacteriostatic or bactericidal activity or efficacy of said antibiotic.

3. The method of claim 1, wherein the terpene is in combination with an antifungal for increasing a fungicidal activity or efficacy of said antifungal.

4. The method of claim 1, wherein said terpene is combined with at least a second terpene selected from ophiobolin A, ophiobolin B and ceroplastol.

5. The method of claim 1, wherein said terpene is combined with betulinic acid or a salt thereof.

6. The method of claim 5, wherein said terpene and said betulinic acid or a salt thereof are in a weight ratio from 1:5 to 5:1.

7. The method of claim 1, wherein said terpene is combined with a steroidal pentacyclic triterpene.

8. The method of claim 1, wherein said terpene is combined with friedelin or a salt thereof, and, wherein said terpene or a salt thereof and said friedelin or a salt thereof are in a weight ratio from 1:5 to 5:1.

9. The method of claim 1, wherein said terpene is combined with betulinic acid or a salt thereof, and with a steroidal pentacyclic triterpene.

10. The method of claim 9, wherein said terpene, said betulinic acid or a salt thereof and said steroidal pentacyclic triterpene are in a weight ratio of 1:1:1.

11. The method of claim 4, wherein the second terpene is ophiobolin A.

12. The method of claim 6, wherein said terpene or a salt thereof or a derivative thereof and said betulinic acid or a salt thereof are in a weight ratio from 1:3 to 3:1.

13. The method of claim 7, wherein the steroidal pentacyclic triterpene is friedelin or a salt thereof.

14. The method of claim 8, wherein said terpene or a salt thereof and said friedelin or a salt thereof are in a weight ratio from 1:3 to 3:1.

15. The method of claim 1, wherein the *Pseudomonas* is *Pseudomonas aeruginosa*, the *Bacillus* is *Bacillus cereus* and the *Trichoderma* is *Trichoderma viride* or *Trichoderma viridescens*.

* * * * *